(12) United States Patent
Anand et al.

(10) Patent No.: US 10,828,424 B2
(45) Date of Patent: Nov. 10, 2020

(54) AUTOMATED DRUG DELIVERY SYSTEMS AND METHODS

(71) Applicant: Alcyone Lifesciences, Inc., Lowell, MA (US)

(72) Inventors: PJ Anand, Lowell, MA (US); Ayesha Arzumand, North Billerica, MA (US); Morgan Brophy, Boston, MA (US); Andrew East, Arlington, MA (US); Gregory Eberl, Acton, MA (US); Deep Arjun Singh, Cambridge, MA (US)

(73) Assignee: ALCYONE LIFESCIENCES, INC., Lowell, MA (US)

(*) Notice: Subject to any disclaimer, the term of this patent is extended or adjusted under 35 U.S.C. 154(b) by 322 days.

(21) Appl. No.: 15/662,416

(22) Filed: Jul. 28, 2017

(65) Prior Publication Data

US 2018/0028761 A1 Feb. 1, 2018

Related U.S. Application Data

(60) Provisional application No. 62/369,361, filed on Aug. 1, 2016, provisional application No. 62/368,797, filed on Jul. 29, 2016.

(51) Int. Cl.
*A61M 5/31* (2006.01)
*A61M 5/315* (2006.01)
(Continued)

(52) U.S. Cl.
CPC .... *A61M 5/31578* (2013.01); *A61M 5/14546* (2013.01); *A61M 5/2033* (2013.01);
(Continued)

(58) Field of Classification Search
CPC .......... A61M 5/31578; A61M 5/14546; A61M 5/2033; A61M 5/3204; A61M 5/19; A61M 5/2046; A61M 2205/33; A61M 2205/3344; A61M 2210/1003; A61M 2230/06; A61M 2205/502; A61M 2205/52
See application file for complete search history.

(56) References Cited

U.S. PATENT DOCUMENTS 4,666,430 A * 5/1987 Brown .............. A61M 5/14526
128/DIG. 12
4,707,906 A 11/1987 Posey
(Continued)

FOREIGN PATENT DOCUMENTS

KR 101200374 B1 11/2012
WO 97/00091 A1 1/1997
WO 2016/026573 A2 2/2016

OTHER PUBLICATIONS

International Search Report and Written Opinion for Application No. PCT/US2017/044286, dated Dec. 21, 2017 (10 pages).

*Primary Examiner* — Amber R Stiles
(74) *Attorney, Agent, or Firm* — Marshall, Gerstein & Borun LLP

(57) ABSTRACT

Automated drug delivery systems and related methods are disclosed herein. In some embodiments, these systems can reduce or eliminate infusion inconsistencies. An exemplary system can include a syringe actuator which can be controlled via electrical, mechanical, pneumatic, and/or hydraulic means to precisely infuse and/or withdraw material from a patient.

20 Claims, 7 Drawing Sheets

(51) Int. Cl.
*A61M 5/145* (2006.01)
*A61M 5/20* (2006.01)
*A61M 5/32* (2006.01)
*A61M 5/19* (2006.01)

(52) U.S. Cl.
CPC ............. *A61M 5/3204* (2013.01); *A61M 5/19* (2013.01); *A61M 5/2046* (2013.01); *A61M 2205/33* (2013.01); *A61M 2205/3344* (2013.01); *A61M 2205/502* (2013.01); *A61M 2205/52* (2013.01); *A61M 2210/1003* (2013.01); *A61M 2230/06* (2013.01)

(56) References Cited

U.S. PATENT DOCUMENTS

| | | | |
|---|---|---|---|
| 5,034,004 A * | 7/1991 | Crankshaw | A61M 5/1452 604/154 |
| 5,312,389 A | 5/1994 | Theeuwes et al. | |
| 6,929,619 B2 | 8/2005 | Fago et al. | |
| 7,632,245 B1 | 12/2009 | Cowan et al. | |
| 9,125,984 B2 | 9/2015 | Friebe et al. | |
| 9,682,193 B2 | 6/2017 | Anand et al. | |
| 2004/0174768 A1 | 9/2004 | Coffeen et al. | |
| 2005/0107697 A1* | 5/2005 | Berke | A61M 5/14546 600/431 |
| 2005/0177111 A1* | 8/2005 | Ozeri | A61M 5/1456 604/154 |
| 2009/0004063 A1 | 1/2009 | Higashihara et al. | |
| 2009/0093792 A1 | 4/2009 | Gross et al. | |
| 2009/0292157 A1 | 11/2009 | Bruce et al. | |
| 2009/0302060 A1 | 12/2009 | Keller | |
| 2010/0004533 A1* | 1/2010 | Duchon | A61M 5/14546 600/431 |
| 2011/0296925 A1* | 12/2011 | Miesel | G01L 19/142 73/718 |
| 2012/0172817 A1 | 7/2012 | Bruggemann et al. | |
| 2013/0274577 A1* | 10/2013 | Amirouche | A61M 5/1723 600/365 |
| 2013/0276785 A1 | 10/2013 | Melker et al. | |
| 2014/0094754 A1 | 4/2014 | Servansky | |
| 2015/0181747 A1* | 6/2015 | Bailey | H05K 7/20736 361/679.48 |
| 2016/0331897 A1 | 11/2016 | Anand et al. | |

\* cited by examiner

AUTOMATED DRUG DELIVERY SYSTEMS AND METHODS

CROSS-REFERENCE TO RELATED APPLICATIONS

The present application claims priority to U.S. Provisional Application No. 62/368,797 filed on Jul. 29, 2016 and U.S. Provisional Application No. 62/369,361 filed on Aug. 1, 2016, each of which is hereby incorporated by reference herein.

FIELD

Automated drug delivery systems and related methods are disclosed herein.

BACKGROUND

There are many instances in which it may be desirable to deliver a drug to a patient. A number of existing drug delivery techniques involve manual infusion of a drug using a plunger-type syringe. These techniques can be vulnerable to user variation, resulting in inconsistencies in infusion volume, infusion pressure, infusion timing, and other parameters. A need exists for improved drug delivery systems and related methods.

SUMMARY

Automated drug delivery systems and related methods are disclosed herein. In some embodiments, these systems can reduce or eliminate infusion inconsistencies. An exemplary system can include a syringe actuator which can be controlled via electrical, mechanical, pneumatic, and/or hydraulic means to precisely infuse and/or withdraw material from a patient.

In some embodiments, a drug delivery system can include a drug delivery device; and an actuator having a syringe disposed therein, the syringe in fluid communication with the drug delivery device; wherein the actuator is configured to exert an actuation force on the syringe to expel material from the drug delivery device; wherein the actuator includes: a first cup; and a second cup rotatably coupled to the first cup; wherein rotation of the first cup relative to the second cup exerts the actuation force on the syringe.

The actuator can include a plurality of syringes disposed therein. The first cup can be threadably connected to the second cup. Rotation of the first cup relative to the second cup in a first direction can exert the actuation force on the syringe to expel material from the drug delivery device. Rotation of the first cup relative to the second cup in a second, opposite direction can exert a second actuation force on the syringe to draw material into the drug delivery device. The actuator can include a motor configured to rotate the first cup relative to the second cup. The delivery device can include a catheter or a needle. A barrel of the syringe can extend through a central opening of the first cup.

In some embodiments, a syringe actuator can include a main body; a plurality of syringes, each having a respective plunger; a cap rotatably coupled to the main body; and a force coupling disposed in the cap; wherein rotation of the cap relative to the main body is effective to select which of the syringe plungers is operably connected to the force coupling.

The force coupling can include a fluid line. Rotation of the cap can place the fluid line in fluid communication with a selected one of the syringe plungers. The force coupling can include a solenoid. Rotation of the cap can align the solenoid with a selected one of the syringe plungers. The main body can be defined by the plurality of syringes. The plurality of syringes can be disposed within one or more cavities formed in the main body. The actuator can include a motor configured to rotate the cap relative to the main body.

In some embodiments, a syringe actuator can include a main body having a proximal portion, an intermediate portion, and a distal portion and defining a cavity having a syringe received therein; and a power cartridge disposed in the main body and operably coupled to a plunger of the syringe such that the power cartridge can advance the plunger distally.

The power cartridge can be operably coupled to the plunger of the syringe such that the power cartridge can retract the plunger proximally. The power cartridge can include a vessel of compressed gas. The syringe can be captured between the intermediate and distal portions of the main body. The actuator can include a control system configured to selectively direct force generated by the power cartridge against the plunger. The power cartridge can be disposed within a cavity defined by the proximal and intermediate portions of the main body. The actuator can include an exhaust module. The exhaust module can include at least one of a muffler and a thermal fin.

In some embodiments, a drug delivery system can include a controller; a drug delivery device; an actuator in fluid communication with the drug delivery device, the actuator including a fluid reservoir having a drug disposed therein; an actuation line connecting the actuator to the controller, the actuation line being configured to transmit from the controller to the actuator at least one of (i) a first actuation force to urge fluid out of the drug delivery device, and (ii) a second actuation force to draw fluid into the drug delivery device.

The drug delivery device can include at least one of a needle and a catheter. In some embodiments, the actuation line does not include a drug. The actuation line can include a flexible cable disposed within an outer sheath, the cable being at least one of axially translatable and axially rotatable relative to the outer sheath. The controller can be configured to be disposed outside of a sterile field while the actuator is disposed within the sterile field. The system can include a user control mounted to the actuator and selectively operable to transmit a signal to the controller. The system can include a signal line configured to transmit information between the controller and the actuator. The drug delivery device can include a sensor communicably coupled to the controller via the signal line. The fluid reservoir can include a syringe. The first actuation force can be effective to move a plunger of the syringe distally and the second actuation force can be effective to move the plunger proximally.

DETAILED DESCRIPTION

Figure 1:
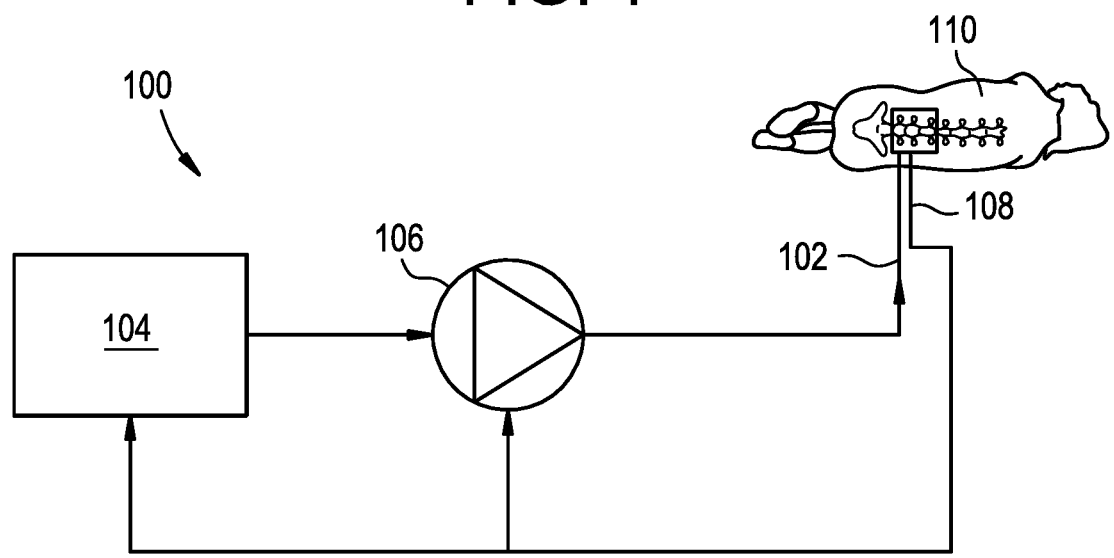
FIG. 1 is a schematic view of a drug delivery system.

Automated drug delivery systems and related methods are disclosed herein. In some embodiments, these systems can reduce or eliminate infusion inconsistencies. An exemplary system can include a syringe actuator which can be controlled via electrical, mechanical, pneumatic, and/or hydraulic means to precisely infuse and/or withdraw material from a patient.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

The term "drug" as used herein refers to any functional agent that can be delivered to a human or animal subject, including hormones, stem cells, gene therapies, chemicals, compounds, small and large molecules, dyes, tracers (for imaging or otherwise), antibodies, viruses, therapeutic agents, oligonucleotides, antisense therapies, etc.

In some embodiments, the systems and methods disclosed herein can provide automated syringe actuation. Automated syringe actuation can be achieved with a hand-held unit that can be positioned close to the patient and controlled directly by a surgeon or other user within the sterile field. The systems and methods disclosed herein can provide the flexibility of automated actuation of multiple syringes or multiple lumens, vials, or reservoirs. The systems and methods described herein can include sensing and/or feedback from a handheld actuator to a controller or console.

In some embodiments, the systems and methods disclosed herein can be used to inject or otherwise deliver a drug to the central nervous system of a patient in coordination with the natural CSF flow. For example, the drug can be injected in a plurality of stages synchronized in phase and/or frequency with the natural CSF pulse. The systems and methods herein can allow for a drug to be delivered more efficiently to a patient than in the case of traditional techniques. For example, a smaller quantity of the drug can be delivered and still reach the target destination, thereby reducing cost and/or possible side effects of delivering a large quantity of the drug.

In some embodiments, the systems and methods disclosed herein can be used in applications where the intended delivery target is not accessible or not accessible in a minimally-invasive manner, but instead more readily-accessible and safer injection sites which are in direct fluid communication with the intended delivery site exist. For example, a drug can be delivered to the intrathecal space of a patient via an injection site in the patient's spine (e.g., a lumbar region, a thoracic region, a cervical region, and so forth) and can be transported via the intrathecal space to a target location that is cranial to the injection site (e.g., the brain or a more-cranial region of the spine, such as a cervical or high thoracic region of the spine). In other embodiments, the drug can be transported to a location that is caudal to the injection site.

In some embodiments, the systems and methods disclosed herein can include fully programmable customized injection and/or aspiration profiles which can be synchronized by real-time monitoring of physiological parameters of the patient, such as heart rate, CSF pressure, CSF pulsation rate, respiration rate, lung capacity, chest expansion and contraction, intrathoracic pressure, intraabdominal pressure, and the like. This can allow the end user to fine-tune injection/aspiration doses per cycle, time length and profile of each microinjection, relative timing (or phase) of microinjections, and other parameters. The systems and methods disclosed herein can include real-time inline pressure sensing for estimating drug delivery efficiency and ensuring patient safety.

In some embodiments, the systems and methods disclosed herein can be capable of providing drug delivery with improved consistency with little or no change to existing protocols or workflows. In some embodiments, the systems and methods disclosed herein can provide real-time confirmation of infusion/delivery success. In some embodiments, the systems and methods disclosed herein can provide a reliable, portable, plug-and-play, disposable, and/or compliant drug delivery platform. In some embodiments, the systems and methods disclosed herein can provide safe infusion of a bolus, e.g., having a volume of at least 0.5 to 30 mL, in a slow, consistent, and/or customizable, e.g., user-specific or patient-specific, patterns. In some embodiments, the systems and methods disclosed herein can provide high-resolution imaging confirmation of delivery.

FIG. 1 is a schematic diagram of an exemplary drug delivery system 100. As shown, the system 100 can include a delivery device 102 (e.g., a catheter, a needle, or the like), a controller 104, and a pump or actuator 106. The system 100 can also include one or more sensors 108. The actuator 106 can be configured to pump, inject, or otherwise deliver material through the delivery device 102 and into a patient 110 (e.g., into an intrathecal space of the patient). The actuator 106 can also be configured to aspirate or remove material from the patient via the delivery device 102. The material that is delivered or removed can be, or can include: a fluid, a drug, a drug-containing fluid, a buffer, CSF, artificial CSF, combinations of the foregoing, and so forth. The actuator 106 can be controlled by the controller 104 to deliver or remove material according to a protocol or profile. The profile can synchronize or otherwise coordinate delivery and/or removal of material with a physiological parameter of the patient, which can be measured by the sensor 108 or otherwise. Exemplary physiological parameters can include heart rate, CSF pressure, CSF pulsation rate, respiration rate, lung capacity, chest expansion and contraction, intrathoracic pressure, intraabdominal pressure, and the like. The controller 104 can be built into the actuator 106, or can be a separate component of the system 100, e.g., a remote console.

One or more components of the delivery system 100 and, in some embodiments, all components of the delivery system, can be implanted in the patient. Implanting some or all of the delivery system 100 can facilitate chronic or long-term drug delivery (e.g., over a period of days, weeks, months, or years) via non-invasive at-home or outpatient procedures.

The delivery device 102 can be a needle, such as a lumbar puncture needle. The delivery device can be a catheter, e.g., an intrathecal or intravascular catheter. The delivery device can be part of a syringe contained within the actuator 106. Exemplary delivery devices are disclosed in in U.S. Pat. No. 9,682,193 issued on Jun. 20, 2017 and entitled "DRUG DELIVERY SYSTEMS AND METHODS" and in U.S. Provisional Application No. 62/437,168 filed on Dec. 21, 2016 and entitled "DRUG DELIVERY SYSTEMS AND METHODS," each of which is hereby incorporated herein by reference in its entirety. The delivery device can be a steerable and/or threadable catheter. The catheter can include a single lumen or a plurality of lumens, e.g., 1-2 lumens. The catheter can include a guidewire or built-in wires for steering the catheter. The catheter can be configured for connection to a syringe actuator for bolus/acute delivery. The catheter can be fully implantable and can include a port that is accessible to inject fluid (e.g., via a needle connected to a syringe or syringe actuator, via a disposable injector system, and so forth). The delivery device can be configured for insertion and/or drug delivery into the cerebrospinal fluid (CSF) or subarachnoid space of the subject's brain or spine.

Figure 2:
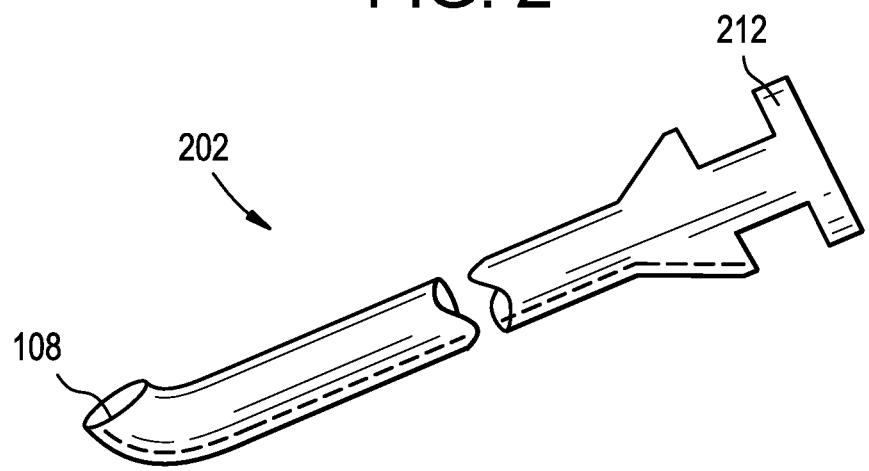
FIG. 2 is a perspective view of a delivery device.

FIG. 2 illustrates an exemplary delivery device 102 in the form of a lumbar puncture needle 202. The needle 202 can be used for delivering a drug to the central nervous system of a patient, to an intrathecal space of the patient, or to other regions or sites within the patient. The needle 202 can include a sensor 108 at the distal tip. The sensor 108 can be a pressure sensor configured to measure the intrathecal pressure before, during, or after infusion. The sensor 108 can be any of a variety of other types of sensors, e.g., of the type described below. The needle 202 can include a luer or other connector or fitting 212 at the proximal end for establishing fluid communication with the needle, e.g., for connecting the needle to the actuator 106 or to a syringe of the actuator.

The actuator 106 can be a syringe actuator having one or more syringes loaded therein. The actuator can be configured to impart an actuation force to the syringe, e.g., to expel material from the syringe or to draw material into the syringe. The actuation force can be applied to a movable plunger component of the syringe. The actuation force can be initiated within the actuator 106, or can be initiated elsewhere, e.g., in the controller 104, and communicated to the actuator. The actuator 106 can include a pump. The actuator 106 can include one or more vials, reservoirs, or containers of fluid, e.g., drug, buffer, etc. The actuator 106 can be configured to supply a drug or a drug-containing fluid to the delivery device 102 and/or to aspirate fluid from the delivery device.

The actuator 106 can include one or more pumps. For example, the actuator 106 can include a plurality of pumps, each being associated with and in fluid communication with a corresponding lumen of the delivery device 102. The pumps can also be associated with and in fluid communication with respective reservoirs for holding a volume of fluid. In some embodiments, the actuator 106 can include first and second syringe pumps coupled to electronic linear actuators configured to advance or retract the plungers of the syringe pumps in response to control signals received from the controller 104. In some embodiments, the actuator 106 can include a peristaltic pump, an auger pump, a gear pump, a piston pump, a bladder pump, etc. One or more portions of the actuator 106 can be implanted in the patient. The actuator 106 can include any of a variety of implantable or extracorporeal pumps. In some embodiments, the actuator 106 can include a fully-implanted, programmable pump and a fully-implanted fluid reservoir containing fluid to be delivered using the system. In some embodiments, the entire actuator 106 can be implantable, e.g., to facilitate chronic treatment methods.

The actuator 106 can be loaded with a custom or off-the-shelf syringe, and can apply a force to the syringe to expel fluid from a distal end of the syringe and/or to draw fluid into the distal end of the syringe. The actuator 106 can hold a single syringe or a plurality of syringes. In the case of multiple syringes, each syringe can be independently or synchronously driven. One or more syringes can be formed integrally with the actuator 106. The actuator 106 can include or can be coupled to the controller 104. For example, the actuator 106 can be connected to the controller 104 via a wired or wireless connection. Alternatively, or in addition, the actuator 106 can be connected to the controller 104 via an actuation line and/or a signal line, as described below. The actuator 106 can include independent syringes for CSF aspiration and for drug infusion. The actuator 106 can include a single syringe used for both CSF aspiration and for drug infusion.

The distal end of the actuator 106 can include or can be coupled to the delivery device 102. For example, the distal end of a syringe loaded into the actuator 106 can define a needle configured for insertion into a patient, or a fluid or other fitting for connecting to the delivery device 102, e.g., via intermediate tubing.

The actuator 106 can be a handheld device. The actuator 106 can include a control that can be actuated by a user. For example, the actuator 106 can include a button, trigger, or other element for providing user control. In some embodiments, the actuator 106 can include a slit or regulator that can be selectively occluded by the user, e.g., to control air pressure applied to a syringe by occluding it different amounts with the user's finger. This can allow for operation of the system in a manual mode.

The system can include various features for providing stability and ergonomics to the user. For example, the actuator 106 can be weighted or can include supports for stabilizing its position with respect to the patient or the user.

The actuator 106 can include a potentiometer or other sensor for determining the position of an operative element of the actuator, e.g., of one or more syringe plungers of the actuator, or drive elements thereof. Position information obtained from the sensor can be communicated to the controller 104 and/or to a user, e.g., via an electronic display of the controller.

The actuator 106 can include various elements or structures for imparting an actuation force to a syringe. The actuation force can be applied to advance a plunger of the syringe to expel material from the syringe. Alternatively, or in addition, the actuation force can be applied to retract a plunger of the syringe to draw material into the syringe. The actuation force can be a linear actuation force. The actuation force can be a rotary actuation force. The actuation force can be generated hydraulically or pneumatically, e.g., by directing liquid or gas under pressure against a syringe plunger or a component operably coupled thereto. The actuation force can be generated mechanically, e.g., via levers, gears, linkages, screws, or the like. The actuation force can be generated electrically or electromagnetically, e.g., via a solenoid, stepper motor, or the like. The actuation force can be generated using any combination of the above principles.

Figure 3:
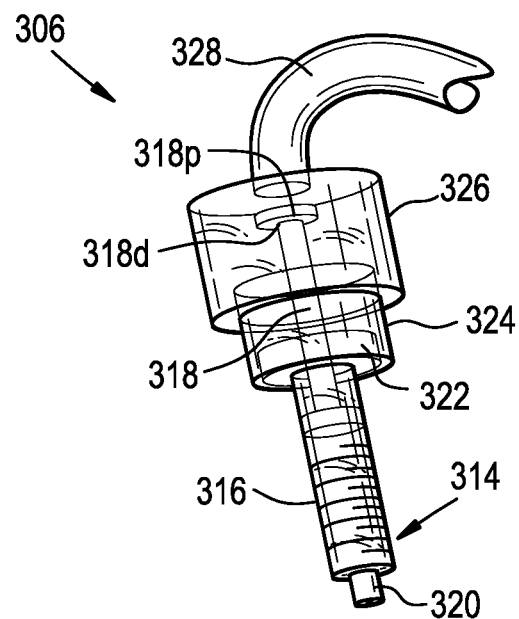
FIG. 3 is a perspective view of a syringe actuator.

FIG. 3 illustrates an exemplary actuator 306. The actuator 306 can be used in the system 100, e.g., to infuse a drug in a controlled and consistent manner with programmable infusion parameters such as pressure, volume, timing, pulsed infusion/aspiration, etc.

The actuator 306 can be used with or can include one or more syringes 314. The syringe 314 can be an off-the-shelf or custom syringe. The syringe 314 can include a barrel 316, a plunger 318 slidably disposed in the barrel, and an outlet port or nozzle 320. The outlet port 320 can be formed in a needle of the syringe, can be configured to attach to a needle, and/or can be a fluid fitting (e.g., a luer fitting) or other coupling. The barrel 316 of the syringe 314 can define a flange or shoulder 322. The plunger 318 of the syringe can include a distal-facing actuation surface 318d and a proximal-facing actuation surface 318p. A force applied to the distal-facing surface 318d can move the plunger 318 proximally relative to the barrel 316 to draw material into the syringe 314. A force applied to the proximal-facing surface 318p can move the plunger 318 distally relative to the barrel 316 to expel material from the syringe 314.

The actuator 306 can include a lower or distal cup 324. The lower cup 324 can include an opening sized to receive the barrel 316 of the syringe 314 therethrough. The opening can be sized to prevent the shoulder 322 of the syringe from passing distally through the opening. Accordingly, a portion of the lower cup 324, e.g., a floor of the lower cup, can contact and bear against the shoulder 322. The actuator 306 can include an upper or proximal cup 326. A portion of the upper cup 326 can contact and bear against the plunger 318 of the syringe 314. For example, a first engagement surface of the upper cup 326 can contact the distal-facing surface 318d of the plunger 318 and a second engagement surface of the upper cup can contact the proximal-facing surface 318p of the plunger. In some arrangements, the upper cup 326 only contacts the proximal-facing surface 318p.

The upper and lower cups 326, 324 can be movable relative to one another to actuate the syringe. A force can be imparted to the actuator 306 to move the upper cup 326 relative to the lower cup 324. The force can be generated in any of the ways described herein, including hydraulically, pneumatically, mechanically, electrically, or using combinations thereof. For example, the lower cup 324 can be threaded into the upper cup 326, or vice-versa, and a hydraulic, pneumatic, or electric motor can be used to impart a rotational force to rotate one cup with respect to the other. The upper and lower cups 326, 324 can be mated to one another via a threaded interface. Relative rotation of the upper and lower cups 326, 324 in a first direction can be effective to move the cups towards one another to expel material from the syringe 314. Relative rotation of the upper and lower cups 326, 324 in a second, opposite direction can be effective to move the cups away from one another to draw material into the syringe 314.

In some embodiments, the lower cup 324 can have a threaded interior and the upper cup can be replaced with a threaded plug rotatably mounted within the lower cup. Accordingly, rotational force imparted to the plug can produce longitudinal translating movement of the plug with respect to the lower cup 324, thereby depressing the plunger 318 to expel material from the syringe 314 and/or lifting the plunger to draw material into the syringe. The actuation force can be provided to the actuator 306 via an actuation line 328. One end of the actuation line 328 can be coupled to the actuator 306 and another end of the actuation line can be coupled to the controller 104 or another component of the system 100. Exemplary actuation lines are described below.

Figure 4:
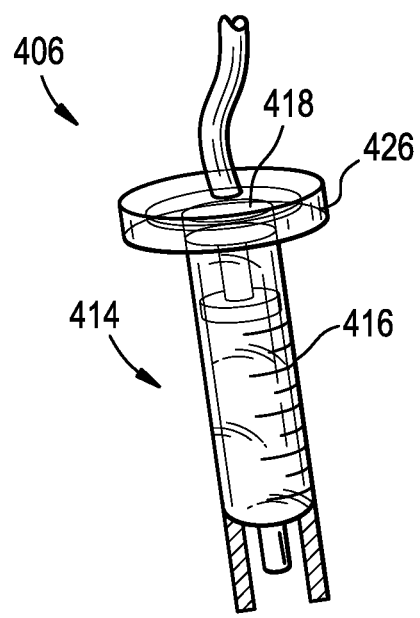
FIG. 4 is a perspective view of another syringe actuator.

FIG. 4 illustrates an exemplary actuator 406. Except as indicated below and as will be readily appreciated by a person having ordinary skill in the art in view of the present disclosure, the structure and operation of the actuator 406 is the same as that of the actuator 306. The actuator 406 can include any of the features or aspects of the actuator 306 described herein.

The actuator 406 can include a compact form-factor customized syringe 414. The barrel 416 and/or the plunger 418 of the syringe 414 can be directly mated to a cup 426 of the actuator 406. For example, the barrel 416 can be fixed to or formed integrally with the cup 426. As another example, the plunger 418 or a bushing disposed therearound can be directly threaded into the cup 426. In other arrangements, the actuator 406 can be pneumatically-driven, e.g., via a pressurized fluid line in communication with the plunger of the syringe.

Figure 5:
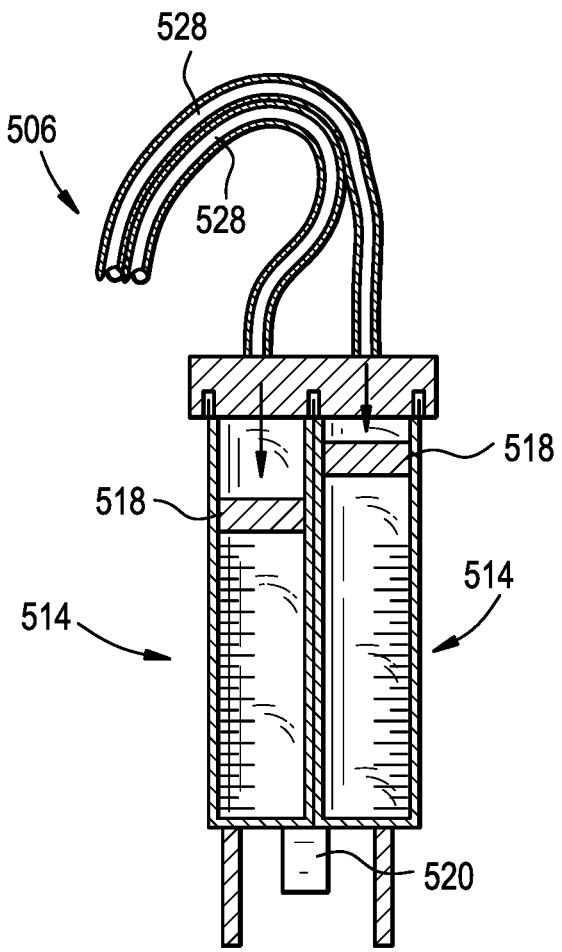
FIG. 5 is a sectional side view of another syringe actuator.

As noted above, any of the actuators described herein can include a plurality of syringes. FIG. 5 illustrates an exemplary multi-channel actuator 506. Except as indicated below and as will be readily appreciated by a person having ordinary skill in the art in view of the present disclosure, the structure and operation of the actuator 506 is the same as that of the actuators 306, 406. The actuator 506 can include any of the features or aspects of the actuators 306, 406 described herein.

The actuator 506 can include first and second syringes 514, each having a respective independently-controlled plunger 518. The actuation forces applied to the plungers 518 can be generated in any of the ways described herein, including hydraulically, pneumatically, mechanically, electrically, or using combinations thereof. For example, the plungers 518 can be pneumatically-controlled and can be coupled to respective independent fluid lines 528, as shown. Application of fluid, e.g., air or $CO_2$, under positive pressure to the plunger 518 can urge the plunger distally to expel material from the syringe 514. Application of fluid under negative or vacuum pressure to the plunger 518 can urge the plunger proximally to draw material into the syringe 514. The fluid reservoirs of the syringes 514 can be in fluid communication adjacent a distal outlet 520 of the actuator 506 as shown, or can be isolated from one another, e.g., by one or more valves such as one-way valves. While two syringes 514 are shown, it will be appreciated that the actuator 506 can include any number of syringes, e.g., 3 or more, 5 or more, 10 or more, etc.

In some embodiments, one syringe, reservoir, or channel of a multi-channel actuator can be filled with a drug and the other with a buffer. The controller can coordinate actuation of the independent plungers to programmatically deliver the drug and buffer to the patient.

In some embodiments, one syringe, reservoir, or channel of a multi-channel actuator can be filled with a first drug and the other with a second drug. The controller can coordinate actuation of the independent plungers to programmatically deliver the first and second drugs to the patient.

In some embodiments, one syringe, reservoir, or channel of a multi-channel actuator can be used to store material to be delivered to the patient and the other reservoir can be used to store material removed from the patient. The controller can coordinate actuation of the independent plungers to programmatically deliver and remove material from the patient.

A multi-channel actuator can include features for selecting to which of a plurality of plungers an actuation force is to be applied. For example, the actuator can include a rotatable mechanism that, when rotated about an axis relative to a main body or other component of the actuator, changes the plunger with which the actuation force is aligned or to which the actuation force is applied. The axis can be a longitudinal axis of the actuator. The axis can be a central longitudinal axis of the actuator.

Figure 6:
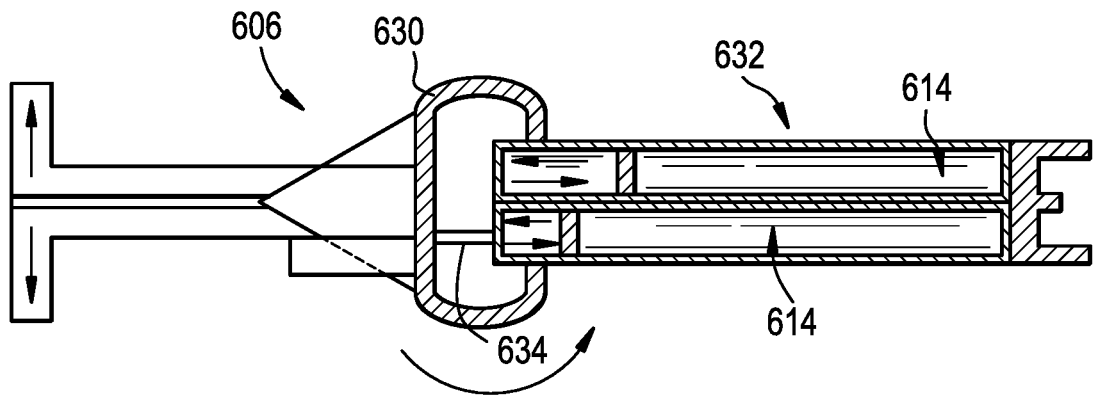
FIG. 6 is a sectional side view of another syringe actuator.

FIG. 6 illustrates an exemplary multi-channel actuator 606 with a rotatable selection mechanism. Except as indicated below and as will be readily appreciated by a person having ordinary skill in the art in view of the present disclosure, the structure and operation of the actuator 606 is the same as that of the actuators 306, 406, 506. The actuator 606 can include any of the features or aspects of the actuators 306, 406, 506 described herein.

The actuator 606 can include a rotatable cap 630. The cap 630 can be rotatably mounted to a main body 632 of the actuator 606, e.g., such that the cap can be rotated relative to the main body about a proximal-distal or longitudinal axis of the actuator 606. The main body 632 can be defined by or can include one or more syringes 614. The cap 630 can include a force coupling 634. Rotation of the cap 630 relative to the main body 632 can be effective to select which of the syringes 614 is aligned with, in contact with, and/or operably coupled to the force coupling 634. The structure of the force coupling 634 can vary depending on the nature of the actuation force used to actuate the syringes 614. The force coupling 634 can be, or can include: a gas line, a fluid line, a charged or pressurized cylinder, a battery, a capacitor, an electrically-conductive element, a solenoid, a spring, a telescopically-expandable strut, a piston, a magnet, and/or combinations thereof. The actuation force can be applied to move the syringe plungers distally, to move the syringe plungers proximally, or to move the syringe plungers both distally and proximally.

Rotation of the cap 632, and thus selection of the syringe 614 to which the actuation force is applied, can be performed manually (e.g., by manual user manipulation) or under the control of the controller 104 or another component of the system 100. For example, the cap 632 can be operably coupled to an electromagnetic drive, a stepper motor, a gear system, or other drive element controlled by the controller 104. The controller 104 can be configured to rotate the cap 632 in accordance with a pre-programmed delivery profile. The controller 104 can be configured to rotate the cap 632 in response to a user input, e.g., pressing of a button or switch on the actuator 606, or interaction with a graphical user interface element displayed on an electronic display of the controller.

Figure 7:
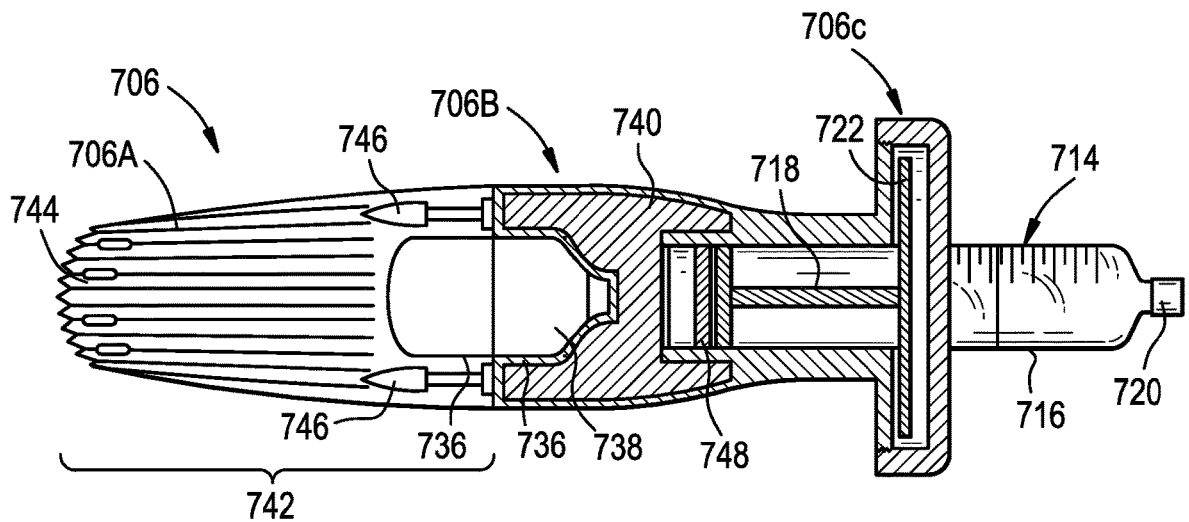
FIG. 7 is a sectional side view of another syringe actuator.

FIG. 7 illustrates an exemplary actuator 706. Except as indicated below and as will be readily appreciated by a person having ordinary skill in the art in view of the present disclosure, the structure and operation of the actuator 706 is the same as that of the actuators 306, 406, 506, 606. The actuator 706 can include any of the features or aspects of the actuators 306, 406, 506, 606 described herein.

The actuator 706 can be an untethered automated infusion handset. The actuator 706 can include a main body having a proximal portion 706A, an intermediate portion 706B, and a distal portion 706C.

The distal portion 706C of the main body can serve as a syringe retainer. The distal portion 706C can be configured to retain a syringe 714 within the actuator 706. The syringe 714 can include a distal outlet port 720, a barrel 716, a flange or shoulder 722, and a plunger or piston 718. The distal portion 706C and the intermediate portion 706B can be configured to capture the flange 722 of the syringe 714 therebetween to secure the syringe to the actuator 706.

The intermediate portion 706B of the main body can define a chamber 736 that houses a power cartridge 738. At least a portion of the chamber 736 can be defined by the proximal portion 706A of the main body. The power cartridge 738 can be any element or structure for providing an actuation force to the plunger 718 of the syringe 714. The power cartridge 738 can be, or can include: a vessel filled with compressed gas, e.g., carbon dioxide. The power cartridge 738 can be, or can include: a gas line, a fluid line, a charged or pressurized cylinder, a battery, a capacitor, an electrically-conductive element, a solenoid, a spring, a telescopically-expandable strut, a piston, a magnet, and/or combinations thereof. The power cartridge 738 can be electromechanical. The power cartridge 738 can include a motor, e.g., a miniature motor, a micro-linear motor, a stepper motor, or the like. The power cartridge 738 can include a battery, e.g., a rechargeable or disposable high performance battery. The power cartridge 738 can include a transmission, gearing, crank, or cam for transferring rotation of the motor into linear movement of the plunger 718.

The actuator 706 can include a control and/or regulation system 740. The control system 740 can be disposed within the intermediate portion 706B of the actuator 706. The control system 740 can control operation of the actuator 706. The control system 740 can control when an actuation force is applied to the plunger 718 and the direction or vector along which the force is applied. For example, the control system 740 can include one or more fluid lines and one or more valves. The control system 740 can selectively open the valves to direct compressed gas from the power cartridge 738 onto the plunger 718, to stop directing gas onto the plunger, to direct gas against a proximal-facing surface of the plunger, to direct gas against a distal-facing surface of the plunger, and so forth. The control system 740 can include a gas piston 748. The gas piston 748 can be coupled to the plunger 718 of the syringe 714. For example, the gas piston 748 can be fixed to the plunger 718 to prevent axial translation therebetween, thereby permitting unidirectional or bi-directional force application to the plunger. The gas piston 748 can be returned proximally in various ways. For example, the gas piston 748 can be returned by compressed gas from the power cartridge 738, manually (e.g., by insertion of a plunger into the actuator 706), under the bias of a spring, by a lever, bolt, or other cocking mechanism, by venturi suction, and so forth.

The actuator 706 can include an exhaust module 742. The exhaust module 742 can be, or can be housed within, the proximal portion 706A of the main body. The exhaust module 742 can include one or more thermal fins 744. The fins 744 can be cross-drilled or vented. The fins 744 can be configured to dissipate some or all of the cooling effect that results from expansion of compressed gas by the actuator 706. The exhaust module 742 can include one or more mufflers 746. The mufflers 746 can be configured to dissipate some or all of the cooling effect and/or reduce some or all of the sound that results from expansion of compressed gas by the actuator 706. The mufflers 746 can be formed from sintered metal. The mufflers 746 can act as an initial cooling dissipater. Touch surfaces of the actuator 706 can be formed from or coated with a thermally-insulating material.

The proximal, intermediate, and/or distal portions 706A, 706B, 706C of the main body can be selectively separable from one another. For example, the portions can be coupled by a threaded interface, a quarter-turn interface, a snap or friction fit interface, or the like. The distal portion 706C can be removed to allow a syringe 714 to be loaded into the actuator 706. The proximal portion 706A or the distal portion 706C can be removed to allow access to the control system 740, e.g., for docking the control system 740 with an external controller or console 104. The control system 740 can be wirelessly docked with the controller or console 104.

The proximal portion 706A can be removed to allow a power cartridge 738 to be replaced or recharged.

The actuator 706 can be docked to the controller or console 104, e.g., via a wireless, wired, or direct electrical coupling to establish functional and/or power communication between the actuator 706 and the controller 104. The actuator 706 can be docked with or without the power cartridge 738 installed. The controller 104 can recharge a battery of the actuator 706 or vice versa. The controller 104 can download programmatic infusion parameters or profiles to the actuator 706 or vice versa. The controller 104 can upload infusion logs, operational data, sensor output information, or other data from the actuator 706, or vice versa. The controller 104 can program the actuator 706, update actuator firmware, and so forth, or vice versa.

Docking can be performed in a cradle or dock, wirelessly, and/or by connecting to a medical-grade mated locking push/pull shrouded pin cable connector with a handle connector recessed in a handle of the actuator 706. Docking can be performed to upload actuator 706 run and diagnostic data, download infusion program data, charge battery, run functional diagnostic checks, perform information exchange, upload case data, review how infusion went, download next set of infusion profile/parameters, etc.

The actuator 706 can be a handheld device. The actuator 706 can be completely decoupled from the controller/console 104, e.g., such that no tube, cable, or other structure extends therebetween.

The actuator 706 can be provided with various accessories. The actuator 706 can include a thermally-insulated "cold pad" for handling a gas cartridge after use. The actuator 706 can include a return plunger insertable into a distal end of the main body to return the gas spring proximally after use. The actuator 706 can include an electrical connection dock or docking station. The actuator 706 can include a grasping tool to assist with cartridge removal. The actuator 706 can include a support arm for mounting the actuator to a table, to the floor, to the patient, to the surgeon or user, or to another support to facilitate hands-free or reduced-strain operation. The support arm can be configured to hold a plurality of actuators 706.

Multiple of the actuators 706 can be used simultaneously to inject and/or withdraw material from the same patient. The multiple actuators 706 can be coordinated by pre-programming, direct cabling, cabling to a common console, wireless synchronization, and/or a client-server or cloud-based model.

The actuator 706 can include one or more user controls or interface elements. For example, the actuator 706 can include tactile surface switches. The actuator 706 can include an electronic display. The actuator 706 can include one or more lights, such as LEDs. The interface elements can communicate device operating parameters and status to a user, e.g., device ready, device operating, pulsatile infusion mode, slow infusion mode, standard infusion mode, infusion complete, alert, etc. The actuator 706 can include operational switches for key override or parameter functions.

Figure 8A:
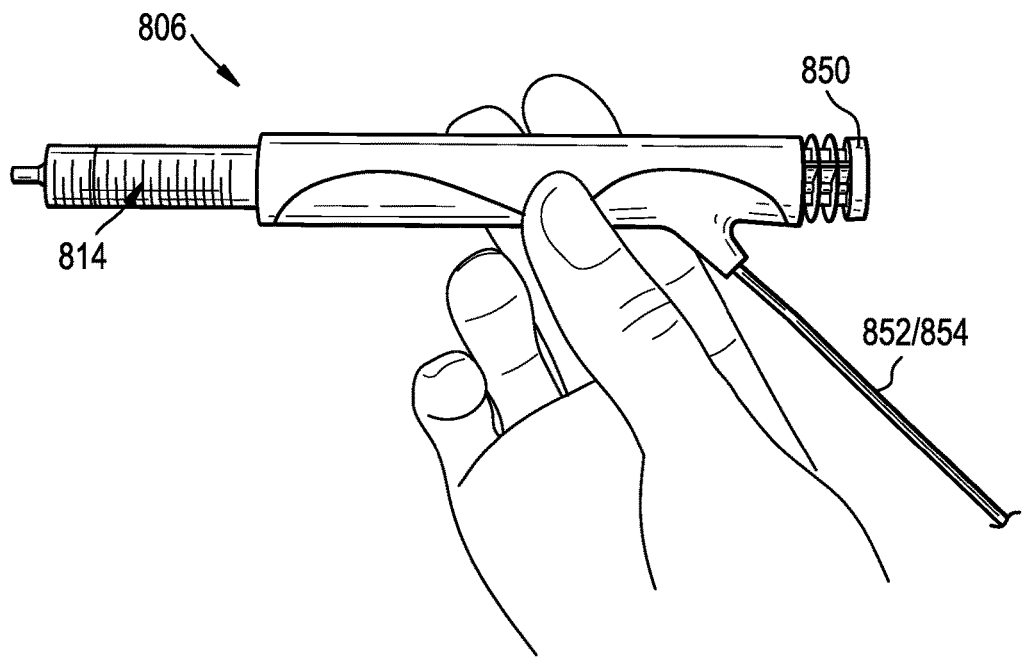
FIG. 8A is a perspective view of another syringe actuator shown with a fluid fitting.
Figure 8B:
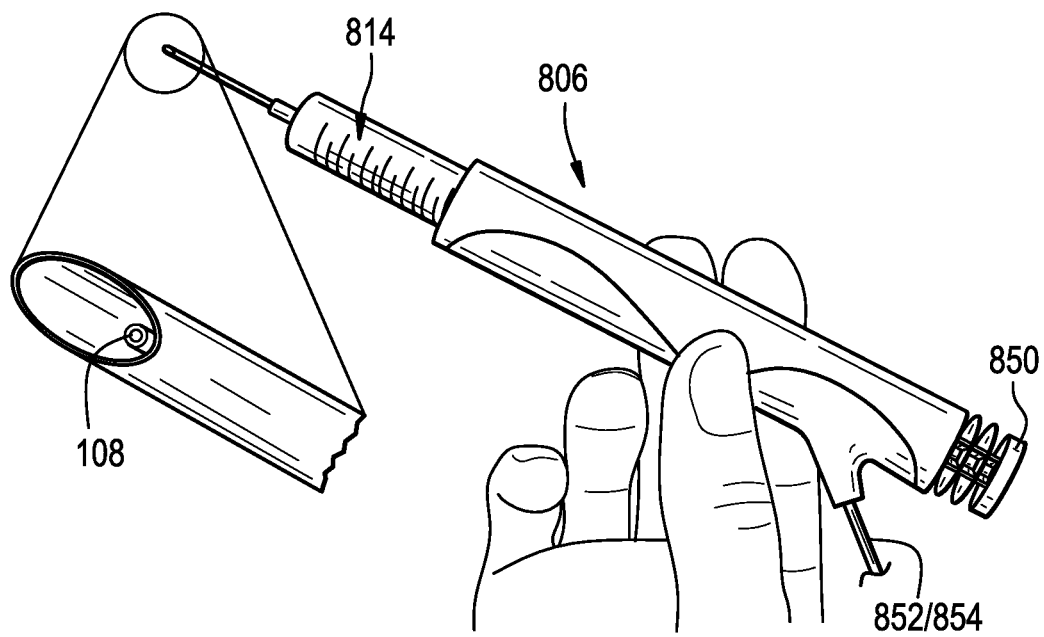
FIG. 8B is a perspective view of the syringe actuator of FIG. 8A shown with a needle.

FIGS. 8A-8B illustrate an exemplary actuator 806. Except as indicated below and as will be readily appreciated by a person having ordinary skill in the art in view of the present disclosure, the structure and operation of the actuator 806 is the same as that of the actuators 306, 406, 506, 606, 706. The actuator 806 can include any of the features or aspects of the actuators 306, 406, 506, 606, 706 described herein.

As shown in FIG. 8A, the actuator 806 can be a small handheld syringe actuator. The actuator 806 can include a main body that defines a cavity sized to receive one or more syringes 814 therein. The syringe 814 can include a distal fluid fitting or other connector, as shown in FIG. 8A, or a distal needle as shown in FIG. 8B. The needle can include an integrated sensor 108, e.g., a pressure sensor. The actuator 806 can include a push button or other control 850. The control 850 can be actuated by a user to begin an infusion, to stop an infusion, or to perform some other control of the actuator 806. The actuator 806 can be operably coupled to the controller 104 via an actuation line 852 and/or a signal line 854, as described below.

The system 100 can include a controller 104 with a processor and a digital display or other user interface for specifying infusion parameters. The controller 104 can control operation of the system 100, e.g., by applying an actuation force or instruction to the actuator 106. The controller 104 can be operably connected to the actuator 106 such that the controller can apply an actuation force to the actuator in an automated manner.

The controller 104 can include a docking station, e.g., for charging an energy source of the actuator 106 such as a gas chamber, battery, spring, or the like, or for downloading or uploading data to or from the actuator.

Figure 9:
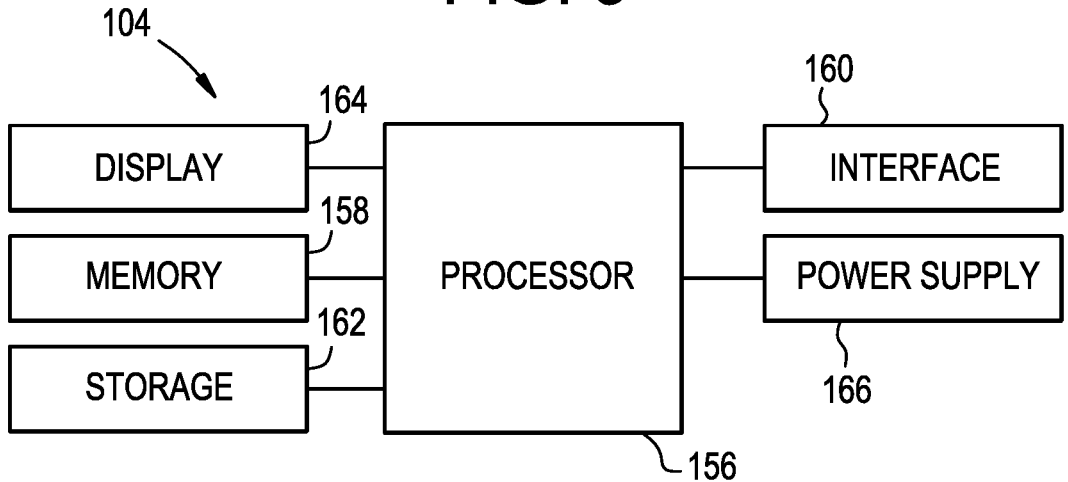
FIG. 9 is a schematic hardware diagram of a controller.

FIG. 9 illustrates a block diagram of the physical components of an exemplary embodiment of the controller 104. Although an exemplary controller 104 is depicted and described herein, it will be appreciated that this is for sake of generality and convenience. In other embodiments, the controller 104 may differ in architecture and operation from that shown and described here. The controller 104 can be a tablet computer, mobile device, smart phone, laptop computer, desktop computer, cloud-based computer, server computer, and so forth. One or more portions of the controller 104 can be implanted in the patient. Delivery control software can execute on the controller 104. The software can execute on a local hardware component (e.g., a tablet computer, smart phone, laptop computer, or the like) or can execute remotely (e.g., on a server or cloud-connected computing device in communications coupling with the controller).

The illustrated controller 104 includes a processor 156 which controls the operation of the controller 104, for example by executing embedded software, operating systems, device drivers, application programs, and so forth. The processor 156 can include any type of microprocessor or central processing unit (CPU), including programmable general-purpose or special-purpose processors and/or any of a variety of proprietary or commercially-available single or multi-processor systems. As used herein, the term processor can refer to microprocessors, microcontrollers, ASICs, FPGAs, PICs, processors that read and interpret program instructions from internal or external memory or registers, and so forth. The controller 104 also includes a memory 158, which provides temporary or permanent storage for code to be executed by the processor 156 or for data that is processed by the processor. The memory 158 can include read-only memory (ROM), flash memory, one or more varieties of random access memory (RAM), and/or a combination of memory technologies. The various components of the controller 104 can be interconnected via any one or more separate traces, physical busses, communication lines, etc.

The controller 104 can also include an interface 160, such as a communication interface or an I/O interface. A communication interface can enable the controller 104 to communicate with remote devices (e.g., other controllers or computer systems) over a network or communications bus (e.g., a universal serial bus). An I/O interface can facilitate communication between one or more input devices, one or more output devices, and the various other components of the controller 104. Exemplary input devices include touch screens, mechanical buttons, keyboards, and pointing devices. The controller 104 can also include a storage device 162, which can include any conventional medium for storing data in a non-volatile and/or non-transient manner. The storage device 162 can thus hold data and/or instructions in a persistent state (i.e., the value is retained despite interruption of power to the controller 104). The storage device 162 can include one or more hard disk drives, flash drives, USB drives, optical drives, various media disks or cards, and/or any combination thereof and can be directly connected to the other components of the controller 104 or remotely connected thereto, such as through the communication interface. The controller 104 can also include a display 164, and can generate images to be displayed thereon. In some embodiments, the display 164 can be a vacuum fluorescent display (VFD), an organic light-emitting diode (OLED) display, or a liquid crystal display (LCD). The controller 104 can also include a power supply 166 and appropriate regulating and conditioning circuitry. Exemplary power supplies include batteries, such as polymer lithium ion batteries, or adapters for coupling the controller 104 to a DC or AC power source (e.g., a USB adapter or a wall adapter).

Figure 10:
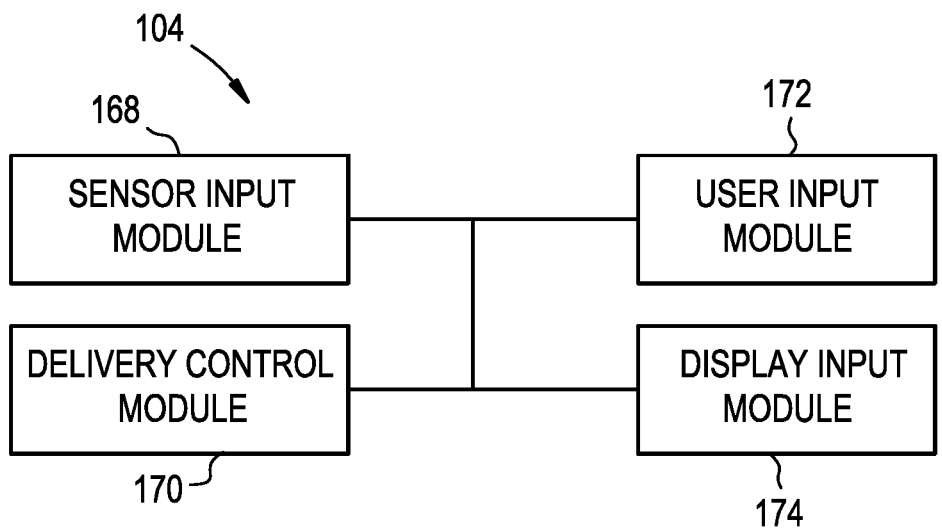
FIG. 10 is a functional block diagram of the controller of FIG. 9.

The various functions performed by the controller 104 can be logically described as being performed by one or more modules. It will be appreciated that such modules can be implemented in hardware, software, or a combination thereof. It will further be appreciated that, when implemented in software, modules can be part of a single program or one or more separate programs, and can be implemented in a variety of contexts (e.g., as part of an embedded software package, an operating system, a device driver, a standalone application, and/or combinations thereof). In addition, software embodying one or more modules can be stored as an executable program on one or more non-transitory computer-readable storage mediums. Functions disclosed herein as being performed by a particular module can also be performed by any other module or combination of modules, and the controller can include fewer or more modules than what is shown and described herein. FIG. 10 is a schematic diagram of the modules of one exemplary embodiment of the controller 104.

As shown in FIG. 10, the controller 104 can include a sensor input module 168 configured to receive information from the sensor(s) 108. The sensor input module 168 can read and interpret output signals supplied from the sensors 108 to the processor 156, e.g., via a general purpose input/output pin of the processor. The sensor input module 168 can optionally perform various processing on the sensor signals, such as frequency detection, phase detection, debouncing, analog-to-digital conversion, filtering, and so forth.

The controller 104 can also include a delivery control module 170 configured to control the pump or actuator 106 to infuse or aspirate fluid from the patient and/or to control the delivery device 102 (e.g., an auger, piston, transducer, ultrasound system, etc.). For example, when an "infuse" instruction is issued, the delivery control module 170 can cause power or an actuation force to be supplied to the actuator 106 to begin pumping infusate through the delivery device 102, or cause an electronically-actuated valve to open such that infusate stored under pressure is placed in fluid communication with the delivery device and flows therethrough. In some embodiments, the delivery control module 170 can be configured to cut off power to the actuator 106, to close a valve, or to otherwise remove or reduce an actuation force supplied to the actuator when a pressure sensor indicates that the pressure in the system has reached a predetermined threshold amount. When an "aspirate" instruction is issued, the delivery control module 170 can cause power or an actuation force to be supplied to the actuator 106 to begin pumping fluid out of the delivery device 102.

The controller 104 can include a user input module 172 configured to receive one or more user inputs, e.g., as supplied by a user via the interface 160. Exemplary user inputs can include infusion parameters, patient information, treatment protocols, and so forth.

The controller 104 can also include a display module 174 configured to display various information to the user on the display 164, such as a graphical or textual user interface, menus, buttons, instructions, and other interface elements. The display module 174 can also be configured to display instructions, warnings, errors, measurements, and calculations.

The controller 104 can be configured to control various infusion and/or aspiration parameters to achieve customized delivery. This can allow the delivery to be tailored based on the therapeutic application. Exemplary parameters that can be controlled by the controller 104 include infusion type, infusion rate, infusion volume, time between infusions, oscillatory rate, infusion and withdraw ratio, infusion phase timing, aspiration type, aspiration rate, time between aspirations, aspiration volume, and so forth.

The sensor 108 can be a single sensor or a plurality of sensors. Exemplary sensors include pressure sensors, electrocardiogram sensors, heart rate sensors, temperature sensors, PH sensors, respiration rate sensors, respiration volume sensors, lung capacity sensors, chest expansion and contraction sensors, intrathoracic pressure sensors, intraabdominal pressure sensors, and the like. One or more of the sensors 108 can be implanted in the patient. One or more of the sensors 108 can be mounted on, inserted through, or formed in or on the delivery device 102. The sensors 108 can also be remote from the delivery device 102. In some embodiments, the sensors 108 can include a pressure sensor disposed in or on the delivery device 102 for measuring CSF pressure adjacent to the delivery device and an ECG sensor for measuring the patient's heart rate. The sensors 108 can be connected (via wires or via a wireless connection) to the sensor input module 168 of the controller 104.

One or more components of the system 100 can be disposed within a sterile field (e.g., in a sterile field defined about the patient). The system 100 can be disposed entirely within the sterile field, or one or more components of the system 100 can be disposed outside of the sterile field.

Figure 11A:
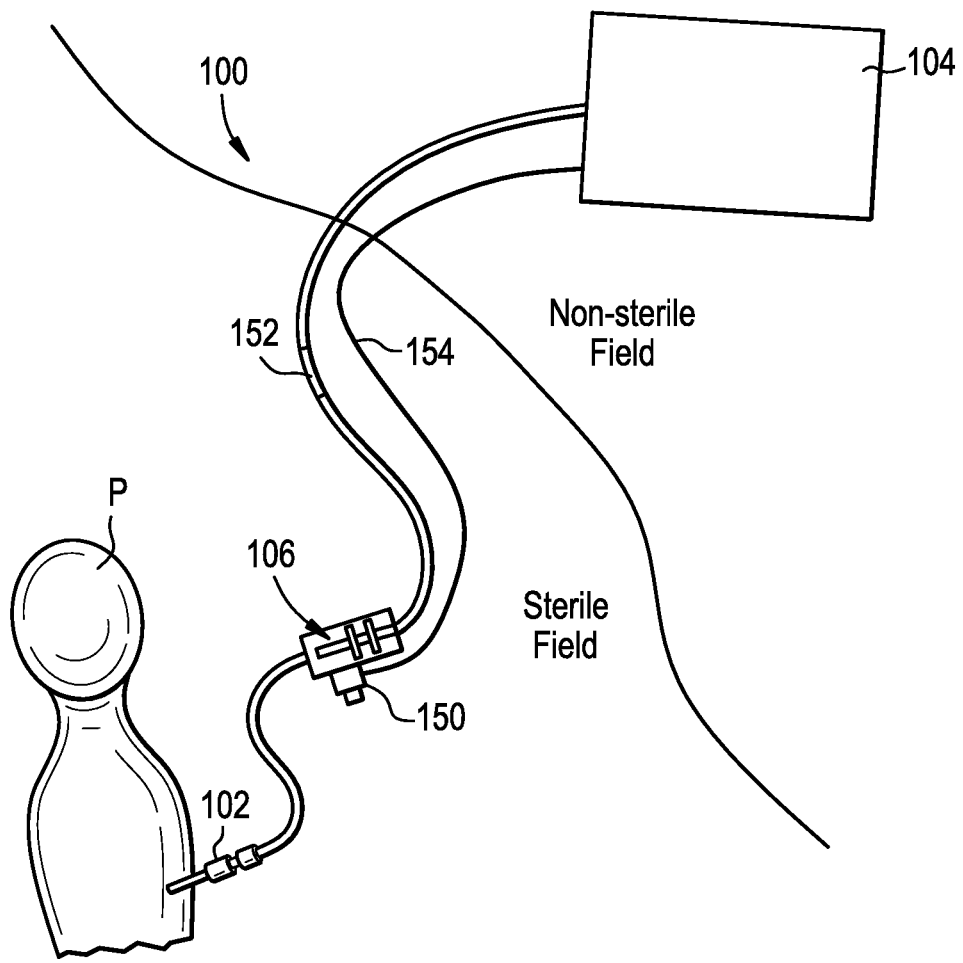
FIG. 11A is a schematic view of a drug delivery system partially disposed within a sterile field and partially disposed outside of the sterile field.

For example, as shown in FIG. 11A, the controller 104 can be disposed remotely from the actuator 106 and the delivery device 102. The controller 104 can be disposed outside the sterile field while the actuator 106 and the delivery device 102 are disposed within the sterile field, e.g., in close proximity to the patient P.

Figure 11B:
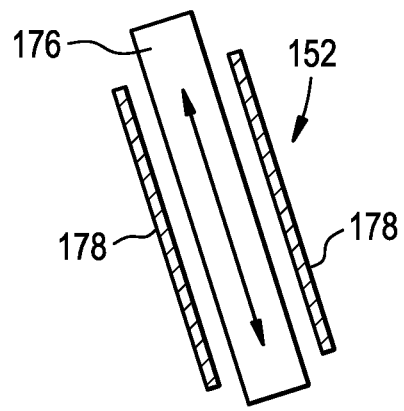
FIG. 11B is a sectional side view of an actuation line of the delivery system of FIG. 11A.

The controller 104 can be coupled to the actuator 106, or a syringe module thereof, by an actuation line 152. The actuation line 152 can be configured to communicate an actuation force generated by the controller 104 to the actuator 106. In other words, the actuation line 152 can translate or transfer actuation energy and/or force from outside the sterile field to inside the sterile field. As shown in FIG. 11B, an exemplary actuation line 152 can include an inner actuator cable, rod, or wire 176 supported by an outer sleeve 178. The actuator cable 176 can have high column strength such that the cable can communicate axial and/or rotational actuation force even when the cable is bent or curved. The outer sleeve 178 can be flexible. The outer sleeve 178 can be braided. The outer sleeve 178 can be axially rigid. In other arrangements, the actuation line 152 can transfer the actuation force via other means, such as pneumatically, hydraulically, mechanically, electrically, etc. In some embodiments, the actuation line 152 does not include any drug, thereby improving the drug volume efficiency of the system.

The controller 104 can be coupled to the actuator 106 by a signal line 154. The signal line 154 can allow the actuator 106 to communicate switch, button, trigger, control, sensor data, infusion/aspiration profiles, diagnostic data, or other instructions, information, or signals back to the controller 104 and vice versa. The signal line 154 can be an electrically conductive wire. The signal line 154 can be a wireless communication link.

The actuator 106 can include a button or other trigger control 150 that can be actuated by the user, e.g., to signal to the controller 104 to begin infusion, stop infusion, begin aspiration, stop aspiration, adjust infusion/aspiration parameters, etc.

The arrangement shown in FIG. 11A can be advantageous in that the line or lines containing the drug or other material delivered to and/or removed from the patient P can be made short, without requiring close proximity between the controller 104 and the actuator 106. This can provide drug volume efficiency. Such an arrangement can also allow for direct actuator 106 control or manipulation from within the sterile field, e.g., to allow a surgeon, patient, or other user in close proximity to the patient to interact with the system 100. In some arrangements, the actuator 106 can be disposed outside of the sterile field and the user control 150 can be disposed within the sterile field. For example, the user control 150 can be provided in a separate housing or a separate component that is operably coupled to the actuator 106.

The controller 104 can be a reusable component. The actuator 106, the actuation line 152, the signal line 154, and/or the delivery device 102 can be reusable or can be disposable.

The systems and methods herein can include any of the features disclosed in U.S. Pat. No. 9,682,193 issued on Jun. 20, 2017 and entitled "DRUG DELIVERY SYSTEMS AND METHODS" and in U.S. Provisional Application No. 62/437,168 filed on Dec. 21, 2016 and entitled "DRUG DELIVERY SYSTEMS AND METHODS," each of which is hereby incorporated herein by reference in its entirety. For example, the systems and methods herein can use pulsatile delivery to coordinate infusion with a physiological parameter of the patient, such as the natural CSF pulsation, heart rate, respiration rate, or combinations thereof.

The systems and methods herein can be semi-automated or fully automated. The systems herein can be fully or partially disposable. The systems and methods herein can be used to treat any human or animal patient, including infants and children. The systems and methods herein can be used with standard lumbar puncture or intrathecal injection/infusion procedures. Infusion parameters can be programmed on site or can be preprogrammed. Infusion parameters can be controlled partially or entirely based on data measured from the patient. The system can be directly connected to AC mains power or other power supply or can be battery operated. The system can include a user input device for controlling operation of the system (e.g., a foot pedal for starting, stopping, or otherwise controlling infusion. The systems and methods herein can be used in conjunction with a lumbar puncture needle or intrathecal catheter. The systems and methods herein can be used for infusion, aspiration, or combinations thereof.

Exemplary drugs that can be delivered using the systems and methods herein can include antisense oligonulceotides, adeno viruses, gene therapies, including AAV and non-AAV, gene editing, gene switching, oncolytic immunotherapies, monoclonal and polyclonal antibodies, stereopure nucleic acids, small molecules, methotrexate, edavarone-conjugate, conotoxin, abomorphine, prednisolone hemisuccinate sodium, carbidopa/levodopa, tetrabenazine, benzodiazepines, such as diazepam and midazolam, alphaxalone or other derivative, cyclophosphamide, idursulfase (Elaprase), iduronidase (Aldurazyme), topotecan, buslfan, and/or combinations thereof.

The systems and methods herein can be used to treat a variety of diseases or conditions, including Parkinson's disease, Friedreich's ataxia, Canavan's disease, amyotrophic lateral sclerosis (ALS), congenital seizures, Dravet syndrome, pain, spinal muscular atrophy (SMA), tauopathies, Huntington's disease, brain/spine/central nervous system (CNS) tumors, inflammation, Hunter syndrome, Alzheimer's disease, hydrocephalus (e.g., therapeutic cure for hydrocephalus), Sanfilippo syndrome, Sanfilippo syndrome type A, Sanfilippo syndrome tybe B, epilepsy, epilepsy pre-visualase, primary central nervous system lymphoma (PCNSL), multiple sclerosis (MS), primary progressive MS (PPMS), acute disseminated encephalomyelitis (ADEM), motor fluctuations in advanced Parkinson's disease patients, acute repetitive seizures (ARS), status epilepticus, enzyme replacement therapy (ERT), and/or neoplastic meningitis.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The systems disclosed herein can be constructed from any of a variety of known materials. Exemplary materials include those which are suitable for use in surgical or medical applications, including metals such as stainless steel, titanium, nickel, cobalt-chromium, or alloys and combinations thereof, polymers such as PEEK, ceramics, carbon fiber, and so forth. The various components of the systems disclosed herein can be rigid or flexible. One or more components or portions of the system can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:
1. A drug delivery system, comprising:
a controller;
a drug delivery device;
an actuator in fluid communication with the drug delivery device, the actuator including a fluid reservoir having a drug disposed therein;

an actuation line connecting the actuator to the controller, the actuation line being configured to transmit from the controller to the actuator: (i) a first actuation force to urge fluid out of the drug delivery device, and (ii) a second actuation force to draw fluid into the drug delivery device; and a user control mounted to the actuator and selectively operable to transmit a signal to the controller.

2. The system of claim 1, wherein the drug delivery device comprises a needle.

3. The system of claim 1, wherein the actuation line does not include a drug.

4. The system of claim 1, wherein the controller is remote from the actuator, such that the controller is configured to be disposed outside of a sterile field while the actuator is disposed within the sterile field.

5. The system of claim 1, further comprising a signal line configured to transmit information between the controller and the actuator.

6. The system of claim 5, wherein the drug delivery device includes a sensor communicably coupled to the controller via the signal line.

7. The system of claim 6, wherein the sensor comprises a pressure sensor.

8. The system of claim 7, wherein the controller is configured to:
receive data from the pressure sensor; and
stop operation of the actuator in response to determining that the data from the pressure sensor indicates a pressure greater than a threshold pressure.

9. The system of claim 1, wherein the fluid reservoir comprises a syringe and wherein the first actuation force is effective to move a plunger of the syringe distally and the second actuation force is effective to move the plunger proximally.

10. The system of claim 1, further comprising one or more sensors operably coupled to the controller, the one or more sensors comprising one or more of:
electrocardiogram sensors; heart rate sensors; temperature sensors; PH sensors, respiration rate sensors; respiration volume sensors; lung capacity sensors; chest expansion and contraction sensors; or pressure sensors.

11. The system of claim 10, wherein the controller is configured to:
receive signals from the one or more sensors; and
process the signals to at least one of: detect a frequency; detect a phase; debounce one of the signals; convert one of the signals from analog to digital; or filter one of the signals.

12. The system of claim 1, wherein the controller comprises:
a processor; and
a memory having instructions stored thereon that cause the processor to perform operations, the operations comprising at least one of: select one of a plurality of infusion types; select an infusion rate; select an infusion volume; select a time between infusions; select an oscillatory rate; select an infusion and withdraw ratio; select an infusion phase timing; select an aspiration type; select an aspiration rate; select a time between aspirations; select an aspiration volume.

13. The system of claim 1, wherein the actuator comprises a plurality of fluid reservoirs.

14. The system of claim 13, wherein the actuation line comprises a plurality of actuation lines connecting individual ones of the plurality of fluid reservoirs to the controller.

15. The system of claim 1, further comprising a display configured to display information to a user.

16. The system of claim 1, further comprising a user input configured to receive input from a user, the input comprising at least one of: infusion parameters; patient information; or treatment protocols.

17. The system of claim 1, wherein the actuator further comprises a valve operable to control flow of fluid from the actuator; and the actuation line being configured to transmit from the controller to the actuator the first actuation force comprises the actuation line being configured to transmit from the controller to the actuator a signal to open the valve.

18. The system of claim 1, wherein the first and second actuation forces are transmitted pneumatically, hydraulically, mechanically, or electrically.

19. The system of claim 1, wherein the drug delivery device comprises a catheter.

20. A drug delivery system, comprising:
a controller;
a drug delivery device;
an actuator in fluid communication with the drug delivery device, the actuator including a fluid reservoir having a drug disposed therein;
an actuation line connecting the actuator to the controller, the actuation line being configured to transmit from the controller to the actuator at least one of (i) a first actuation force to urge fluid out of the drug delivery device, and (ii) a second actuation force to draw fluid into the drug delivery device,
wherein the actuation line comprises a flexible cable disposed within an outer sheath, the cable being at least one of axially translatable and axially rotatable relative to the outer sheath to provide the at least one of (i) the first actuation force to urge fluid out of the drug delivery device, and (ii) the second actuation force to draw fluid into the drug delivery device.

* * * * *